United States Patent
Allan

[19]

[11] Patent Number: 5,969,235
[45] Date of Patent: Oct. 19, 1999

[54] SYSTEM AND METHOD FOR MEASURING SCALE DEPOSITION INCLUDING A TUNING FORK FOR USE IN THE SYSTEM AND THE METHOD

[75] Inventor: Graeme Allan, Mullaloo, Australia

[73] Assignee: Nalco Chemical Company, Naperville, Ill.

[21] Appl. No.: 09/109,636

[22] Filed: Jul. 2, 1998

[51] Int. Cl.[6] ................................................. G01N 33/00
[52] U.S. Cl. ............................................................ 73/61.62
[58] Field of Search ............................... 73/61.62, 61.71, 73/61.75, 24.01, 24.03, 32 A, 53.01, 61.45, 61.79

[56] References Cited

U.S. PATENT DOCUMENTS

| | | |
|---|---|---|
| 3,848,187 | 11/1974 | Rohrback et al. . |
| 4,002,057 | 1/1977 | Kannapell et al. ..................... 73/61.62 |
| 4,138,878 | 2/1979 | Holmes et al. .................... 73/61.62 X |
| 4,142,402 | 3/1979 | Mattioli et al. ......................... 73/61.62 |
| 4,426,880 | 1/1984 | Walters et al. . |
| 4,541,278 | 9/1985 | Marsh et al. . |
| 5,013,488 | 5/1991 | Abadi et al. . |
| 5,627,310 | 5/1997 | Johnson ................................. 73/61.73 |
| 5,734,098 | 3/1998 | Kraus et al. . |

FOREIGN PATENT DOCUMENTS 1508612  4/1978  United Kingdom .

Primary Examiner—Benjamin R. Fuller
Assistant Examiner—Jewel Thompson
Attorney, Agent, or Firm—Hill & Simpson

[57] ABSTRACT

A system and a method for measuring scale deposition in a process system are provided. Also, a tuning fork used as a sensor for measuring scale deposition and the process that is used with the system and method are also set forth. The tuning fork detects vibrations which have a virtually linear relationship with the scale deposition on the tuning fork. The change in frequency of vibration is, therefore, measured and may be monitored and used to change a signal which, in turn, may run or control a pump for adding necessary components, such as anti-scalant products, to the process stream. The resulting measurement is conducted in real time and, therefore, scale formation in a mineral processing system or other system in which the tuning fork is implemented may also be conducted in real time.

17 Claims, 1 Drawing Sheet

SYSTEM AND METHOD FOR MEASURING SCALE DEPOSITION INCLUDING A TUNING FORK FOR USE IN THE SYSTEM AND THE METHOD

BACKGROUND OF THE INVENTION

The present invention generally relates to a system and method for measuring scale deposition as well as a tuning fork used with the system and method. More specifically, the present invention relates to measurement of scale deposition in a liquid or process stream and controlling input of product, such as an anti-scalant, based on the deposition that is measured in the liquid or the process stream.

It is, of course, generally known to use tuning forks in many industries. One common use of a tuning fork is to use the same as a digital switch. In certain industries, the tuning fork may be used to measure liquid in tanks or other closed systems where it is necessary to determine liquid levels.

In many industrial applications, such as mineral processing, scale or other components are deposited within the system. Such deposits may often become problematic. For example, fouling of the system and components or causing conditions of low flow in the system may often result.

A need, therefore, exists for a system and a method for measuring scale deposition as well as an instrument to implement the same within certain applications, such as, but not limited to, mineral processing applications. Further, a need exists to automatically add products, such as anti-scalants, to a process stream as a result of such measurements.

SUMMARY OF THE INVENTION

The present invention provides a system and a method for measuring scale deposition. In addition, the present invention provides a tuning fork used as an instrument within the system and method for measuring scale deposition.

To this end, in an embodiment of the present invention, a tuning fork for measuring scale deposition is provided. The tuning fork has a stem having a first end and a second end defining a length. A first tine and a second tine are integrally formed with the stem at the second end. An electronic unit is associated with the stem wherein the electronic unit senses a change due to build-up of scale deposition on the first tine or the second tine and converts the sensed change to an output signal.

In an embodiment, the sensed change is a change in frequency of vibration.

In an embodiment, the electronic unit is a piezo electric cell.

In an embodiment, the handle and the first tine and the second tine are constructed of stainless steel material.

In an embodiment, the sensed change, in turn, changes a signal capable of running a pump.

In another embodiment of the present invention, a system is provided for measuring scale deposition. The system has a tuning fork having a stem integrally formed with a first tine and a second tine extending from the stem. An electronic unit associated with the tuning fork is provided wherein the electronic unit senses a change due to build-up of scale deposition on the tuning fork and converts the sensed change to an output signal.

In an embodiment, the electronic unit is a piezo electric cell in the tuning fork.

The tuning fork can be constructed from any metal. In an embodiment the tuning fork is constructed from stainless steel material.

In an embodiment, a pump receives the output signal from the electronic unit.

In an embodiment, the change to the tuning fork is a change in frequency of vibration.

In an embodiment, a controller receives the output signal from the tuning fork and converts the output signal to a control signal.

In another embodiment of the present invention, a method is provided for measuring scale deposition. The method comprises the steps of: providing a tuning fork having a stem and tines integrally formed with the stem; providing a sensor associated with the tuning fork; immersing the tuning fork in a liquid; and measuring the scale deposition on the tuning fork.

In an embodiment, the sensor creates vibration in the fork.

In an embodiment, the sensor is a piezo electric cell.

In an embodiment, the sensor measures a change in frequency.

In an embodiment, an output signal is produced indicative of the scale deposition on the tuning fork.

In an embodiment, a pump is controlled based on the scale deposition measured on the tuning fork.

In an embodiment, data is logged based on the measured scale deposition on the tuning fork.

In an embodiment, the measuring of the scale deposition occurs in real time.

In an embodiment, a dose rate of the product to input to the liquid is maintained based on the measured scale deposition.

In an embodiment, the method and device are used to measure viscosity of a liquid.

It is, therefore, an advantage of the present invention to provide a system, a method and a tuning fork for measuring scale deposition.

Another advantage of the present invention is to provide a system, a method and a tuning fork for measuring scale deposition that is simple to implement.

A further advantage of the present invention is to provide a system, a method, and a tuning fork for measuring scale deposition that measures the same in real time.

Moreover, an advantage of the present invention is to provide a system, a method and a tuning fork for measuring scale deposition that is simple to use.

A still further advantage of the present invention is to provide a system, a method and a tuning fork for measuring scale deposition that provides an output signal to control a pump or other like device.

And, another advantage of the present invention is to provide a system, a method and a tuning fork for measuring scale deposition that is capable of logging data for future review and/or troubleshooting.

Yet another advantage of the present invention is to provide a system, a method and a tuning fork for accurately measuring scale deposition.

A still further advantage of the present invention is to provide a system, a method and a tuning fork for measuring scale deposition that is relatively inexpensive to implement.

And, another of the present invention is to provide a system, a method and a tuning fork for measuring scale deposition that is capable of monitoring and controlling the dosage of anti-scalant products.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a tuning fork capable of use in a system that includes a liquid or other fluid that is often subjected to scale being deposited into the system. The tuning fork has particular applications within a mineral processing system wherein deposits of scale often cause problems with fouling of the system components and/or creating low flow conditions. Of course, the tuning fork may be applied to any system where it is important to measure scale and control the build-up of scale deposits in the system. The tuning fork can also be used to measure the viscosity of a liquid. A system and method for measuring scale deposition using the tuning fork of the present invention are also described hereinafter.

Figure 1:
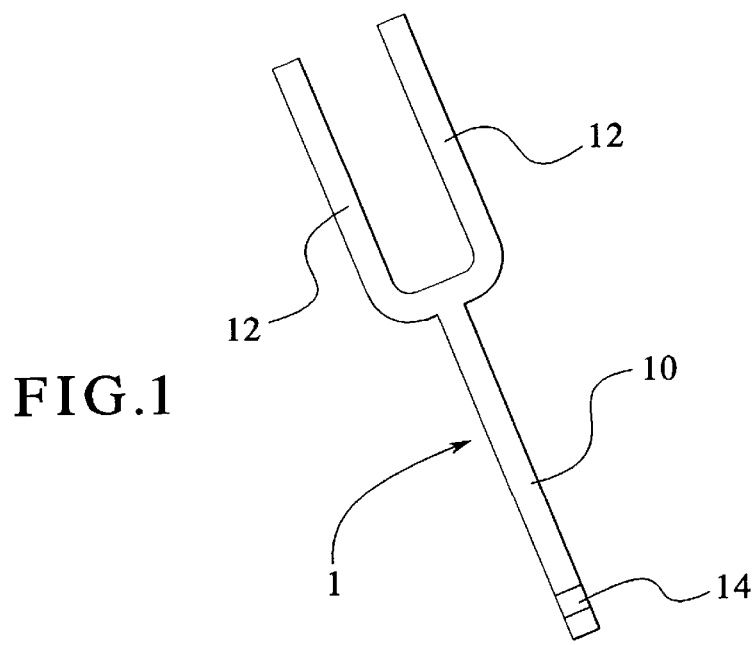
FIG. 1 generally illustrates a perspective view of an embodiment of a tuning fork of the present invention.

Referring now to FIG. 1, a tuning fork 1 of the present invention is generally illustrated. The tuning fork 1 includes a stem or handle 10 integrally formed with tines 12. Preferably, the tuning fork 1 is a stainless steel probe-type instrument. A tuning fork 1 may also be made of Hastelloy or may be coated in ECTFE which is particularly suitable for use of the tuning fork 1 in systems or processes in which corrosive liquids are present. The structure and materials of the tuning fork 1 may, of course, vary according to the application in which the tuning fork 1 is implemented. The tuning fork 1 may, preferably, be constructed of a material similar to or compatible with the system in which the tuning fork 1 is used.

In use, the tines 12 of the tuning fork 1 are immersed in a liquid or slurry during use. The tuning fork 1 measures deposition of scale within a process system. The tuning fork 1, therefore, acts as a sensor in use of the system and method for detecting scale deposition. To this end, a piezo electric cell 14 is provided in the tuning fork 1 which creates vibration in the tines 12 of the fork 1. As previously set forth, the tines 12 of the tuning fork 1 may be immersed in a liquid or slurry. Deposits of scale may build on the tines of the tuning fork 1 resulting in a change in frequency of vibration of the tines 12 which, in turn, is sensed by the tuning fork 1. As a result, a quantity or level or amount of scale deposition may be measured and a signal may be provided indicative thereof. That is, the amount of scale deposition is directly related to the change in frequency and is virtually linearly related.

To this end, the change in frequency may be converted into a measurable signal, e.g. 4–20 mA. When the tuning fork 1 is initially immersed in a liquid or slurry, a frequency is initially measured. This is a zero point. As scale builds up on the tines 12 of the tuning fork 1, the mass of the tuning fork 1 increases and, hence, the frequency decreases. The vibrational signal sensed by the tuning fork 1 may be sent to a controller or processor 16 which converts the signal to the 4–20 mA signal which, in turn, can run, for example, a dosing pump 18. Additionally, the signals may be sent, for example, to a memory 20 and/or a display 22 such that the data may be logged for future review of, for example, the rate at which scale deposition takes place in the system. As a result, future review and troubleshooting of the system may take place, and problems with the system may be detected earlier and/or prevented.

Figure 2:
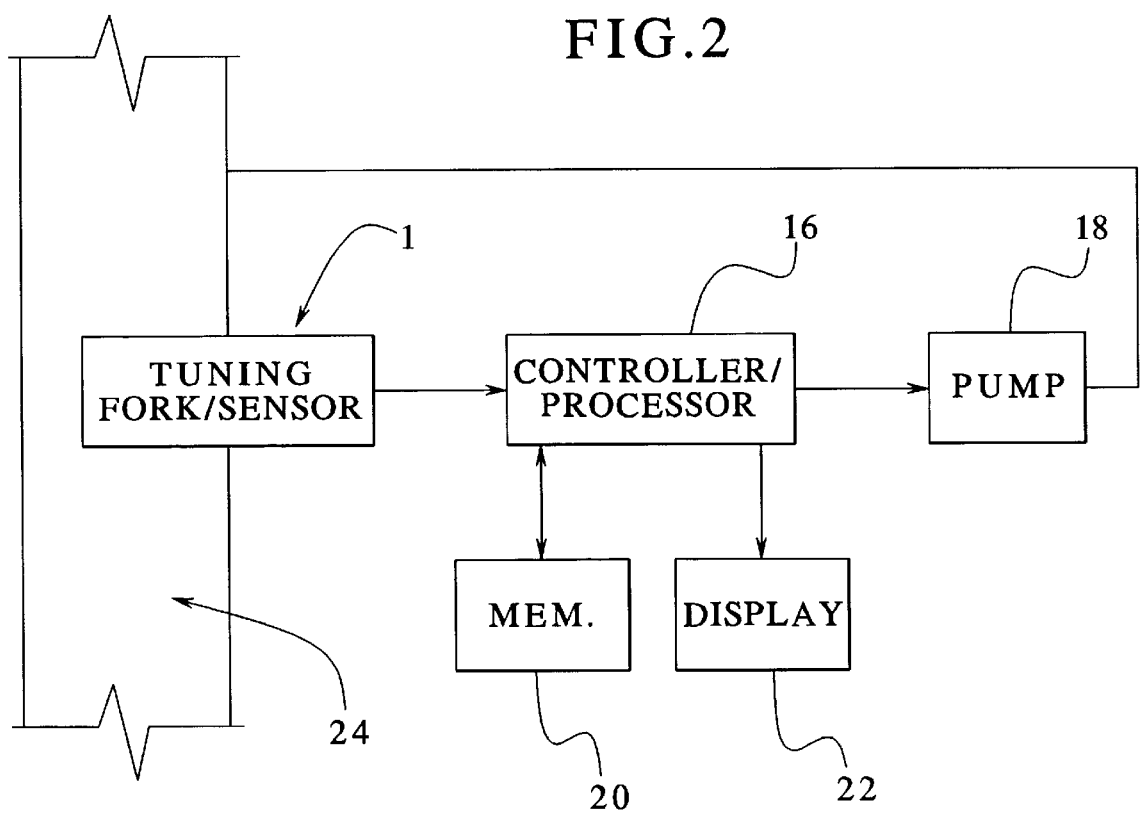
FIG. 2 illustrates a black box diagram of an embodiment of a system for measuring scale deposition using the tuning fork shown and described with reference to FIG. 1.

As shown in FIG. 2, a process stream 24 is provided in which the system are implemented. The tuning fork 1 and its incorporated sensor 14 are immersed in the process stream 24 of the particular application in which scale deposition requires measurement and monitoring.

In addition to the foregoing, the data that is input to the controller/processor 16 may be used to develop algorithms for running the pump 18 based on the data logged in the memory 20 or the data that is received in real time from the tuning fork 1. As a result, projections may be made regarding time in which service may be necessary or, alternatively, when system components may require replacement due to fouling or the like. Also, low flow conditions in the system may also be detected and appropriate maintenance or other required service may be implemented.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A tuning fork for measuring scale deposition, the fork comprising:

a stem having a first end and a second end defining a length;

a first tine and a second tine integrally formed with the stem at the second end; and an electronic unit associated with the stem, wherein the electronic unit senses a change due to build-up of scale deposition on the first tine or the second tine and converts the sensed change to an output signal, and the sensed change, in turn, changes a signal capable of running a pump.

2. The tuning fork of claim 1 wherein the sensed change is a change in frequency of vibration.

3. The tuning fork of claim 1 wherein the electronic unit is a piezo electric cell.

4. The tuning fork of claim 1 wherein the stem and the first tine and the second tine are constructed of stainless steel material.

5. A system for measuring scale deposition, the system comprising:

a tuning fork having a stem integrally formed with a first tine and a second tine extending from the stem;

an electronic unit associated with the tuning fork, wherein the electronic unit senses a change due to build-up of scale deposition on the tuning fork and converts the sensed change to an output signal; and a pump receiving the output signal from the electronic unit.

6. The system of claim 5 wherein the electronic unit is a piezo electric cell in the tuning fork.

7. The system of claim 5 wherein the tuning fork is constructed of stainless steel material.

8. The system of claim 5 wherein the change to the tuning fork is a change in frequency of vibration.

9. The system of claim 5 further comprising:

a controller receiving the output signal from the tuning fork and converting the output signal to a control signal.

10. A method for measuring scale deposition, the method comprising the steps of:

providing a tuning fork having a stem and tines integrally formed with the stem;

providing a sensor associated with the tuning fork;

immersing the tuning fork in a liquid;

measuring the scale deposition in the tuning fork; and controlling a pump based on the scale deposition measured on the tuning fork.

11. The method of claim 10 wherein the sensor creates vibration in the fork.

12. The method of claim 10 wherein the sensor is a piezo electric cell.

13. The method of claim 10 wherein the sensor measures a change in frequency.

14. The method of claim 10 further comprising the step of:

producing an output signal indicative of the scale deposition on the tuning fork.

15. The method of claim 10 further comprising the step of:

logging data based on the measured scale deposition on the tuning fork.

16. The method of claim 10 wherein the measuring of the scale deposition occurs in real time.

17. The method of claim 10 further comprising the step of:

maintaining a dose rate of a product to input to the liquid based on the measured scale deposition.

\* \* \* \* \*